(12) United States Patent
Pleschke

(10) Patent No.: US 7,148,365 B2
(45) Date of Patent: Dec. 12, 2006

(54) PROCESS FOR PREPARING 5-BROMO-2,2-DIFLUOROBENZO-1,3-DIOXOLES

(75) Inventor: Axel Pleschke, Köln (DE)

(73) Assignee: Lanxess Deutschland GmbH, Leverkusen (DE)

( * ) Notice: Subject to any disclaimer, the term of this patent is extended or adjusted under 35 U.S.C. 154(b) by 0 days.

(21) Appl. No.: 11/127,535

(22) Filed: May 12, 2005

(65) Prior Publication Data

US 2005/0272942 A1 Dec. 8, 2005

(30) Foreign Application Priority Data

May 14, 2004 (DE) ................. 10 2004 024 012

(51) Int. Cl.
*C07D 301/10* (2006.01)
(52) U.S. Cl. .................................................... 549/534
(58) Field of Classification Search ................ 549/434
See application file for complete search history.

(56) References Cited

U.S. PATENT DOCUMENTS

| 4,895,871 A | 1/1990 | Lutomski et al. ............ 514/469 |
| 5,194,628 A | 3/1993 | Ackermann et al. ......... 548/526 |
| 5,281,718 A | 1/1994 | Ackermann et al. ......... 548/526 |
| 5,312,800 A | 5/1994 | Rempfler .................... 504/283 |
| 5,420,301 A | 5/1995 | Ackermann et al. ......... 549/213 |

OTHER PUBLICATIONS

Cherry, G. et al: "Elecrophilic bromination of phenol ethers in superacid solution using alkali bromide" TETRAHEDRON LETTERS, Bd. 31, Nr. 14, 1990, Seiten 2007-2010, XP002344442 "Seite 2008".

*Primary Examiner*—Amelia A. Owens
(74) *Attorney, Agent, or Firm*—Jennifer R. Sang

(57) ABSTRACT

The invention relates to a process for preparing 5-bromo-2,2-difluorobenzo-1,3-dioxoles and to the use thereof for preparing medicaments and crop protection agents.

7 Claims, No Drawings

PROCESS FOR PREPARING 5-BROMO-2,2-DIFLUOROBENZO-1,3-DIOXOLES

The invention relates to a process for preparing 5-bromo-2,2-difluorobenzo-1,3-dioxoles and to the use thereof for preparing medicaments and crop protection agents.

5-Bromo-2,2-difluorobenzo-1,3-dioxoles play an important role as precursors for active agrochemical and pharmaceutical ingredients; see also EP 333 658 A and WO 93/24483.

For the preparation of 5-bromo-2,2-difluorobenzo-1,3-dioxoles, only unsatisfactory methods are known to date. For instance, U.S. Pat. No. 4,895,871 describes a bromination of 2,2-difluorobenzo-1,3-dioxole with elemental bromine in toxic carbon tetrachloride. The yield is also very low at 50%, so that this process cannot be considered for industrial purposes.

There is thus a need for a process which enables the preparation of 5-bromo-2,2-difluorobenzo-1,3-dioxoles on the industrial scale in a simple manner and in good yields.

A process has now been found for preparing compounds of the formula (I)

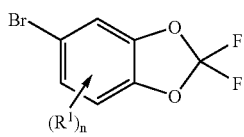

in which
R$^1$ is C$_1$–C$_4$-alkyl, C$_1$–C$_4$-fluoroalkyl, C$_1$–C$_4$-alkoxy, C$_1$–C$_4$-fluoroalkoxy, bromine, chlorine or fluorine and
n is 0 or 1,
which is characterized in that compounds of the formula (II)

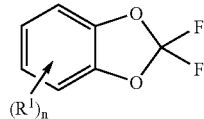

are reacted with bromine in the presence of at least two Friedel-Crafts catalysts of which one is hydrogen fluoride.

The scope of the invention encompasses all radical definitions, parameters and illustrations above and listed hereinbelow, specified in general or within areas of preference, in any combination with one another, i.e. also between the particular areas and areas of preference.

Alkyl and alkoxy are in each case independently a straight-chain, cyclic, branched or unbranched alkyl and alkoxy radical respectively, and the radicals mentioned may optionally be further substituted by C$_1$–C$_4$-alkoxy radicals.

C$_1$–C$_4$-Alkyl is, for example and with preference, methyl, ethyl, n-propyl, isopropyl, or tert-butyl.

C$_1$–C$_4$-Alkoxy is, for example and with preference, methoxy, ethoxy, n-propoxy, isopropoxy and n-butoxy.

Fluoroalkyl and fluoroalkoxy are in each case independently a straight-chain, cyclic, branched or unbranched alkyl radical and alkoxy radical respectively, each of which is substituted singly, multiply or fully by fluorine atoms.

For example, C$_1$–C$_4$-fluoroalkyl is trifluoromethyl, 2,2,2-trifluoroethyl, pentafluoroethyl, nonafluorobutyl and heptafluoroisopropyl.

For example, C$_1$–C$_4$-fluoroalkoxy is trifluoromethoxy, 2,2,2-trifluoroethoxy, pentafluoroethoxy, nonafluorobutoxy and heptafluoroisopropoxy.

The preferred substitution patterns are defined hereinbelow:
R$^1$ is more preferably methyl, ethyl, n-propyl, chlorine, fluorine and bromine, most preferably chlorine or fluorine.
n is preferably 0 or 1, more preferably 0.

Preferred compounds of the formula (II) are 2,2-difluorobenzo-1,3-dioxole and 5-chloro-2,2-difluorobenzo-1,3-dioxole.

Preferred compounds of the formula (II) are 5-bromo-2,2-difluorobenzo-1,3-dioxole and 6-chloro-5-bromo-2,2-difluorobenzo-1,3-dioxole.

The process according to the invention is carried out in the presence of at least two Friedel-Crafts catalysts of which one is hydrogen fluoride. It is clear to those skilled in the art that both components can combine to form protic acids without this being mentioned explicitly in each case.

Suitable Friedel-Crafts catalysts in addition to hydrogen fluoride are, for example, Lewis acids such as BF$_3$, BCl$_3$, FeCl$_3$, FeBr$_3$, SbCl$_3$, SbCl$_5$, SbBr$_3$, SnCl$_4$, ZnCl$_2$, ZnBr$_2$, TiCl$_2$, TiCl$_4$, TiBr$_4$, ZrCl$_4$, MoBr$_4$, MoO$_3$, CuCl$_2$, Cu$_2$Cl$_2$, BeCl$_2$, GeCl$_3$, TeCl$_2$, TeCl$_4$, TICl$_3$, Brønsted acids such as fluorosulphonic acid, chlorosulphonic acid, metals such as iron, cerium, copper or molybdenum. Preferred Friedel-Crafts catalysts are BF$_3$, BCl$_3$, FeCl$_3$, SnCl$_4$, ZnCl$_2$, TiCl$_4$ and MoO$_3$, more preferred are BF$_3$, BCl$_3$, TiCl$_4$ and MoO$_3$, even more preferred is TiCl$_4$.

The molar ratio of Friedel-Crafts catalysts which are not hydrogen fluoride to compounds of the formula (I) may, for example, be 0.1 to 10, but preferably 0.1 to 3 and more preferably 0.5 to 2. Larger amounts are possible but uneconomic.

The molar ratio of hydrogen fluoride to compounds of the formula (I) may, for example, be 0.1 to 1000, but preferably 1 to 10 and more preferably 1.5 to 5. Larger amounts are possible but uneconomic.

The molar ratio of bromine to compounds of the formula (I) may, for example, be 0.5 to 1.2. Larger amounts are possible but are accompanied by falling selectivity for monobrominated products.

The reaction temperature may, for example, be −30 to 90° C., preferably −20 to 80° C., more preferably 0 to 20° C., and the reaction pressure 0.5 to 100 bar, preferably 0.9 to 12 bar.

The metering sequence between compounds of the formula (I), Friedel-Crafts catalysts and bromine is arbitrary, but preference is given to adding bromine last for selectivity reasons.

Owing to the corrosive action of hydrogen fluoride, the reaction should be carried out in stainless steel or Monel apparatus.

Preference is given to effecting the workup by initially distilling off excess bromine, hydrogen fluoride and, if appropriate, Friedel-Crafts catalyst, or removing them by phase separation, and purifying the remaining product, if appropriate by crystallization or distillation. The originally removed mixture of excess bromine, hydrogen fluoride and, if appropriate, Friedel-Crafts catalyst may be recycled back into the reaction without further workup.

In the inventive manner, compounds of the formula (I) may be obtained in high purity and yield in a simple manner.

The compounds of the formula (I) preparable in accordance with the invention are suitable in particular for use in a process for preparing medicaments, agrochemicals or intermediates thereof.

EXAMPLES

Example 1

A stainless steel autoclave was initially charged with 95 ml of hydrogen fluoride, 14.8 g of titanium tetrachloride and 300 g of 5-chloro-2,2-difluorobenzodioxole at 0° C. After the mixture has been stirred for 20 minutes, 249 g of bromine were metered in at 0–10° C. The hydrogen bromide which has been formed was decompressed at 0.5 bar via a condenser cooled to −15° C. On completion of addition, the mixture was stirred at 10° C. for a further 1 hour and at 20° C. for a further 1 hour. Subsequently, under a slightly reduced pressure, the hydrogen fluoride was distilled off and condensed. The residue was discharged onto 900 g of ice and taken up with dichloromethane after the ice has melted. The dichloromethane solution was washed with bicarbonate solution, dried and distilled. After a small first fraction of 5-chloro-2,2-difluorobenzodioxole, 312 g of 5-bromo-6-chloro-2,2-difluorobenzodioxole having a melting point of 95° C./16 mbar were obtained. The yield based on converted 5-chloro-2,2-difluorobenzodioxole was 88.7%.

$^1$H NMR (400 MHz, CDCl$_3$): 7.32 (s, 1H), 7.19 (s, 1H)

Example 2

Analogously to Example 1, 300 g of difluorobenzodioxole in 115 ml of hydrogen fluoride were reacted with 303 g of bromine in the presence of 18 g of titanium tetrachloride. After workup, 380 g of 5-bromo-2,2-difluorobenzodioxole were obtained; boiling point 74–75° C./16 mbar. Yield: 62% of theory.

When the procedure was repeated, it was possible to achieve a yield of 70%.

The invention claimed is:

1. Process for preparing compounds of the formula (I)

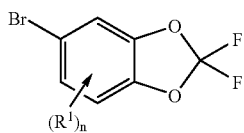

(I)

in which

R$^1$ is C$_1$–C$_4$-alkyl, bromine, chlorine or fluorine and n is 0 or 1, comprising reacting compounds of the formula (II)

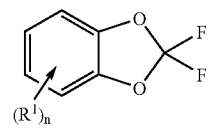

with bromine in the presence of at least two Friedel-Crafts catalysts of which one is hydrogen fluoride.

2. Process according to claim 1, characterized in that R$^1$ in formula (I) is methyl, ethyl, n-propyl, chlorine, fluorine and bromine, and n is 0 or 1.

3. Process according to claim 1, characterized in that the Friedel-Crafts catalysts used in addition to hydrogen fluoride are BF$_3$, BCl$_3$, FeCl$_3$, FeBr$_3$, SbCl$_3$, SbBr$_3$, SbCl$_5$, SnCl$_4$, ZnCl$_2$, ZnBr$_2$, TiCl$_2$, TiCl$_4$, TiBr$_4$, ZrCl$_4$, MoBr$_4$, MoO$_3$, CuCl$_2$, Cu$_2$Cl$_2$, BeCl$_2$, GeCl$_3$, TeCl$_2$, TeCl$_4$, TlCl$_3$, fluorosulphonic acid, chlorosulphonic acid, iron, cerium, copper or molybdenum.

4. Process according to claim 1, characterized in that the molar ratio of Friedel-Crafts catalysts which are not hydrogen fluoride to compounds of the formula (I) is 0.1 to 10.

5. Process according to claim 1, characterized in that the molar ratio of hydrogen fluoride to compounds of the formula (I) is 0.1 to 1000.

6. Process according to claim 1, characterized in that the molar ratio of bromine to compounds of the formula (I) is 0.5 to 1.2.

7. Process according to claim 1, characterized in that, in the metering sequence between compound of the formula (I), Friedel-Crafts catalysts and bromine, bromine is added last.

\* \* \* \* \*